US00PP23844P2

(12) United States Plant Patent
Barends

(10) Patent No.: US PP23,844 P2
(45) Date of Patent: Aug. 20, 2013

(54) ***NEMESIA* PLANT NAMED 'FINEMANGSTRAW'**

(50) Latin Name: *Nemesia hybrida*
Varietal Denomination: Finemangstraw

(75) Inventor: Eveline Barends, De Lier (NL)

(73) Assignee: Fides B.V., De Lier (NL)

( * ) Notice: Subject to any disclaimer, the term of this patent is extended or adjusted under 35 U.S.C. 154(b) by 68 days.

(21) Appl. No.: 13/373,670

(22) Filed: Nov. 23, 2011

(51) Int. Cl.
*A01H 5/00* (2006.01)

(52) U.S. Cl.
USPC ..... Plt./458

(58) Field of Classification Search
USPC ..... Plt./458
See application file for complete search history.

*Primary Examiner* — Susan McCormick Ewoldt
(74) *Attorney, Agent, or Firm* — C. A. Whealy

(57) ABSTRACT

A new and distinct cultivar of *Nemesia* plant named 'Finemangstraw', characterized by its upright, outwardly spreading and uniformly mounded growth habit; freely branching and flowering plant habit; large red-colored flowers that are fragrant; relatively tolerant to high temperatures; and good garden performance.

1 Drawing Sheet

Botanical designation: *Nemesia hybrida.*
Cultivar denomination: 'FINEMANGSTRAW'.

BACKGROUND OF THE INVENTION

The present invention relates to a new and distinct cultivar of *Nemesia* plant, botanically known as *Nemesia hybrida* and hereinafter referred to by the name 'Finemangstraw'.

The new *Nemesia* plant is a product of a planned breeding program conducted by the Inventor in De Lier, The Netherlands. The objective of the breeding program is to create new *Nemesia* plants with good vigor and attractive flower coloration.

The new *Nemesia* plant is a naturally-occurring branch mutation of *Nemesia hybrida* 'Kirine-15', disclosed in U.S. Plant Pat. No. 18,270. The new *Nemesia* plant was discovered and selected by the Inventor on a single flowering plant of 'Kirine-15' within a population of plants of 'Kirine-15' in a controlled greenhouse environment in De Lier, The Netherlands in April, 2009.

Asexual reproduction of the new *Nemesia* plant by terminal cuttings in a controlled environment in De Lier, The Netherlands since April, 2009 has shown that the unique features of this new *Nemesia* plant are stable and reproduced true to type in successive generations.

SUMMARY OF THE INVENTION

Plants of the new *Nemesia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Finemangstraw'. These characteristics in combination distinguish 'Finemangstraw' as a new and distinct *Nemesia* plant:

1. Upright, outwardly spreading and uniformly mounded growth habit.
2. Freely branching and flowering plant habit.

3. Large bright red-colored flowers that are fragrant.
4. Relatively tolerant to high temperatures.
5. Good garden performance.

Plants of the new *Nemesia* can be compared to plants of the parent, 'Kirine-15'. Plants of the new *Nemesia* differ primarily from 'Kirine-15' in flower color as plants of 'Kirine-5' have orange-colored flowers.

Plants of the new *Nemesia* can also be compared to plants of the *Nemesia hybrida* 'Intrairedtwo', disclosed in U.S. Plant Pat. No. 23,061. In side-by-side comparisons conducted in De Lier, The Netherlands, plants of the new *Nemesia* differed primarily from plants of 'Intrairedtwo' in the following characteristics:

1. Plants of the new *Nemesia* were not as trailing as plants of 'Intrairedtwo'.
2. Plants of the new *Nemesia* flowered earlier than plants of 'Intrairedtwo'.

BRIEF DESCRIPTION OF THE PHOTOGRAPH

The accompanying colored photograph illustrates the overall appearance of the new *Nemesia* plant showing the colors as true as it is reasonably possible to obtain in colored reproductions of this type. Colors in the photograph may differ slightly from the color values cited in the detailed botanical description which accurately describe the colors of the new *Nemesia* plant.

The photograph comprises a side perspective view of a typical flowering plant of 'Finemangstraw' grown in a container.

DETAILED BOTANICAL DESCRIPTION

Plants used for the aforementioned photograph and following description were grown under environmental conditions and cultural practices which closely approximate commercial production conditions during the summer and autumn in 12-cm containers in a glass-covered greenhouse in De Lier, The Netherlands. During the production of the plants, day temperatures ranged from 17° C. to 30° C. and night temperatures ranged from 16° C. to 18° C. Plants were pinched about two weeks after planting and were eight weeks old when the photograph and description were taken. In the following description, color references are made to The Royal Horticultural Society Colour Chart, Fifth Edition, except where general terms of ordinary dictionary significance are used.

Botanical classification: *Nemesia hybrida* 'Finemangstraw'.

Parentage: Naturally-occurring branch mutation of *Nemesia hybrida* 'Kirine-15', disclosed in U.S. Plant Pat. No. 18,270.

Propagation:

*Type*.—By terminal cuttings.

*Time to initiate roots, summer and winter*.—About seven days at 22° C.

*Time to produce a rooted young plant, summer*.—About twelve days at 22° C. to 30° C.

*Time to produce a rooted young plant, winter*.—About two weeks at 20° C. to 25° C.

*Root description*.—Medium in thickness, fibrous; greyed white in color.

*Rooting habit*.—Freely branching; moderately dense.

Plant description:

*Plant and growth habit*.—Upright, outwardly spreading and uniformly mounded growth habit; freely branching habit with lateral branches potentially forming at every node; pinching enhances lateral branch development; vigorous growth habit.

*Plant height*.—About 25 cm.

*Plant diameter*.—About 32.5 cm.

Lateral branch description:

*Length*.—About 25 cm.

*Diameter*.—About 2.5 mm.

*Internode length*.—About 3.2 cm.

*Strength*.—Strong.

*Aspect*.—Upright to outwardly spreading.

*Texture*.—Smooth, glabrous.

*Color*.—Close to 144A.

Foliage description:

*Arrangement*.—Opposite, simple; sessile.

*Length*.—About 4 cm.

*Width*.—About 1 cm to 2 cm.

*Shape*.—Lanceolate.

*Apex*.—Acute.

*Base*.—Cuneate.

*Margin*.—Serrate.

*Texture, upper and lower surfaces*.—Smooth, glabrous.

*Venation pattern*.—Pinnate; arcuate.

*Color*.—Developing leaves, upper surface: Close to 137B. Developing leaves, lower surface: Close to 137C. Fully expanded leaves, upper surface: Close to 147A; venation, close to 147B. Fully expanded leaves, lower surface: Close to 147B; venation, close to 147B.

Flower description:

*Flower arrangement and flowering habit*.—Zygomorphic bilabiate flowers arranged on terminal racemes; flowering acropetally towards the apex; flowers face upright and outwardly; freely flowering habit with about 30 to 35 flowers per raceme.

*Flower longevity*.—Flowers last about four to seven days on the plant; flowers not persistent.

*Fragrance*.—Moderately fragrant; floral, pleasant.

*Natural flowering season*.—In The Netherlands, plants flower from spring to fall, flowering continuous during this period; plants will flower year-round if temperatures are higher than 10° C.; plants begin flowering about five to seven weeks after planting. Inflorescence height: About 8 cm to 9.5 cm. Inflorescence diameter: About 4.5 cm.

*Flower height*.—About 2.2 cm.

*Flower diameter*.—About 1.8 cm.

*Flower depth*.—About 1.5 cm.

*Flower buds*.—Shape: Ovoid. Length: About 9 mm. Diameter: About 6 mm. Color: Close to 146A.

*Petals*.—Arrangement: Five petals; four upper petals are fused at base to form an upright lobed and arched banner lip; lower petal modified into a larger lip with convex oval protuberance with serves as a pollinator nectar guide and landing platform. Shape: Oval to rounded. Apex: Rounded. Margin: Entire; lower lip, slightly sinuate. Length: Upper petals: About 2.2 cm. Lower petal: About 1.2 cm. Width: Upper petals: About 5 mm. Lower petal: About 1.5 cm. Texture, upper and lower surfaces: Smooth, glabrous. Color, upper petals: When opening, upper surface: Close to 47C. When opening, lower surface: Close to 161C. Fully opened, upper surface: Close to 44A. Fully opened, lower surface: More grey than 60B. Color, lower petal: When opening, upper surface: Close to 47C. When opening, lower surface: Close to 161C. Fully opened, upper surface: Close to 41A. Fully opened, lower surface: More grey than 60B.

*Sepals*.—Arrangement: Calyx star-shaped with five sepals fused at the base. Shape: Lanceolate. Apex: Acute. Margin: Entire. Length: About 4 mm. Width: About 1 mm. Texture, upper and lower surfaces: Pubescent. Color, upper and lower surfaces: Close to 137B.

*Peduncles*.—Length: About 3.5 cm. Diameter: About 2 mm. Angle: Erect to about 45° from vertical. Strength: Strong. Texture: Scattered pubescence. Color: Close to 137C.

*Pedicels*.—Length: About 1.5 cm. Diameter: About 1 mm. Angle: About 45° from peduncle axis. Strength: Moderately strong. Texture: Pubescent. Color: Close to 137C.

*Reproductive organs*.—Stamens: Quantity: Four per flower. Filament length: About 1.5 mm to 3.5 mm. Filament color: Close to 155D. Anther shape: Oval. Anther length: About 1 mm. Anther color: Close to 163A. Pollen amount: Scarce. Pollen color: Close to 161A. Pistils: Quantity: One per flower. Pistil length: About 3 mm. Style length: About 1 mm. Style color: Close to 145B. Stigma shape: Rounded. Stigma color: Close to 145B. Ovary color: Close to 145A. Seeds and fruits: Seed and fruit development have not been observed on plants of the new *Nemesia*.

Pathogen/pest resistance: Plants of the new *Nemesia* have not been observed to be resistant to pests and pathogens common to *Nemesia*.

Garden performance: Plants of the new *Nemesia* have been observed to tolerate wind and rain and have good garden performance.

Temperature tolerance: Plants of the new *Nemesia* have been observed to tolerate temperatures from about 4° C. to about 35° C.

It is claimed:

1. A new and distinct *Nemesia* plant named 'Finemangstraw' as illustrated and described.

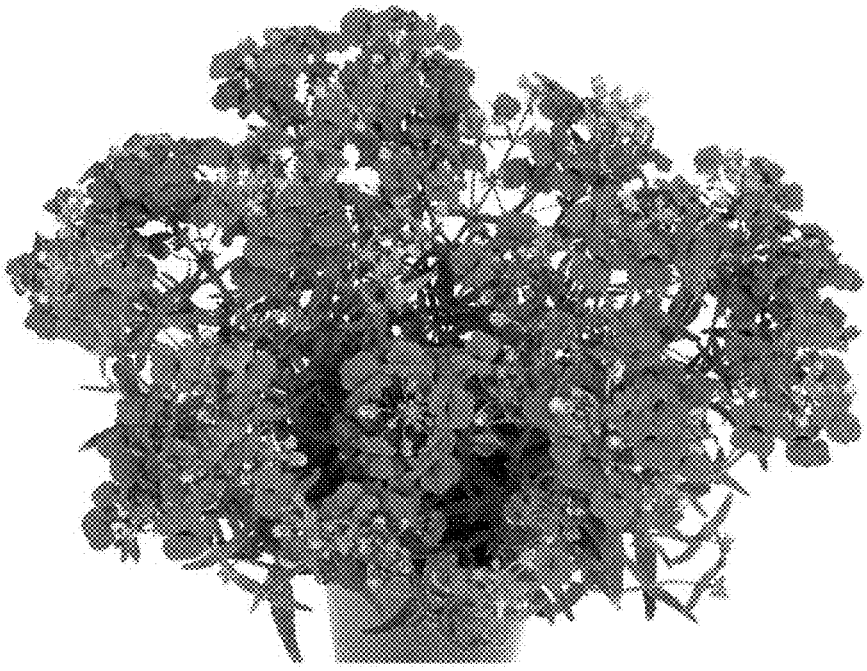

* * * * *